(12) United States Patent
Roh et al.

(10) Patent No.: US 11,937,879 B2
(45) Date of Patent: Mar. 26, 2024

(54) APPARATUS, SYSTEM, AND METHOD FOR IMPLANTING SURGICAL MATERIAL

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael J. Baker, Georgia, VT (US)

(73) Assignee: IX INNOVATION LLC, Seattle, WA (US)

( * ) Notice: Subject to any disclaimer, the term of this patent is extended or adjusted under 35 U.S.C. 154(b) by 0 days.

(21) Appl. No.: 17/749,086

(22) Filed: May 19, 2022

(65) Prior Publication Data

US 2023/0329790 A1   Oct. 19, 2023

Related U.S. Application Data

(63) Continuation of application No. 17/723,404, filed on Apr. 18, 2022.

(51) Int. Cl.
| | |
|---|---|
| *A61B 34/10* | (2016.01) |
| *A61B 90/00* | (2016.01) |
| *A61M 37/00* | (2006.01) |
| *G16H 20/40* | (2018.01) |

(52) U.S. Cl.
CPC ............ *A61B 34/10* (2016.02); *A61B 90/361* (2016.02); *A61M 37/00* (2013.01); *G16H 20/40* (2018.01); *A61B 2034/108* (2016.02)

(58) Field of Classification Search
CPC ........ A61B 2034/104; A61B 2034/108; A61B 2034/2055; A61B 34/10; A61B 34/20; A61B 2034/105; A61B 2017/00203; A61B 2017/00207; A61B 2034/2051; A61B 2034/2068; A61B 2090/3983; A61B 90/361; A61F 2/2875; A61F 2/30942; A61F 2002/30948; A61F 2002/30952; A61F 2002/3095; A61F 2002/30985;
(Continued)

(56) References Cited

U.S. PATENT DOCUMENTS

| | | | | |
|---|---|---|---|---|
| 5,769,092 A | * | 6/1998 | Williamson, Jr. | G05B 19/4099 128/923 |
| 11,304,812 B1 | * | 4/2022 | Khalid | A61F 2/2875 |

(Continued)

*Primary Examiner* — Brandy S Lee
(74) *Attorney, Agent, or Firm* — FisherBroyles, LLP; Jeremy P. Sanders

(57) ABSTRACT

A system for implanting surgical material in a patient's body is disclosed. The system comprises a two-dimensional (2D) laser cutter network comprising a 2D laser cutter and a processor. The processor is configured to perform the steps of capturing an image of an open area of a patient's body and processing a drug implant substrate to create a customized drug implant substrate. The customized drug implant may be created based on the captured image to correspond with the open area of the patient's body. The drug implant substrate is shaped using the 2D laser cutter. The processor is further configured to perform the steps of placing the customized drug implant substrate in the open area of the patient's body and sealing the open area after placing the customized drug implant substrate in the open area.

19 Claims, 7 Drawing Sheets

(58) Field of Classification Search
CPC ..... A61F 2002/4632; A61F 2250/0067; G16H 20/40; A61M 37/00; G05B 19/4099
See application file for complete search history.

(56) References Cited

U.S. PATENT DOCUMENTS

| | | | |
|---|---|---|---|
| 2001/0051761 A1* | 12/2001 | Khadem | A61B 1/00009 600/117 |
| 2012/0041446 A1* | 2/2012 | Wong | A61F 2/30756 606/86 R |
| 2017/0014169 A1* | 1/2017 | Dean | A61B 34/10 |

* cited by examiner

| 3RD PARTY 2D LASER SHAPE DATABASE ||||||
| --- | --- | --- | --- | --- |
| PATIENT NAME | DATE | SHAPE IDENTIFIED FOR SURGICAL OPENING | IMAGE OF SURGICAL OPENING | ACCURACY SCORE |
| ALEX | 20/11/2020 | IMAGE 1 | IMAGE 21 | 96% |
| BARRIE | 18/08/2020 | IMAGE 2 | IMAGE 22 | 98% |
| CATHERINE | 6/07/2021 | IMAGE 3 | IMAGE 33 | 94% |
| DARWIN | 19/2/2021 | IMAGE 4 | IMAGE 44 | 92% |
| ELLE | 12/12/2020 | IMAGE 5 | IMAGE 55 | 96% |

FIG. 2A

| LOCAL DATABASE ||||||
| --- | --- | --- | --- | --- | --- |
| PATIENT NAME | DATE | SHAPE IDENTIFIED FOR SURGICAL OPENING | IMAGE OF SURGICAL OPENING | ACCURACY SCORE | PROCEDURE |
| ALEX | 20/11/2020 | IMAGE 1 | IMAGE 21 | 96% | BRAIN SURGERY |
| BARRIE | 18/08/2020 | IMAGE 2 | IMAGE 22 | 98% | BRAIN SURGERY |
| CATHERINE | 6/07/2021 | IMAGE 3 | IMAGE 33 | 94% | BRAIN SURGERY |
| DARWIN | 19/2/2021 | IMAGE 4 | IMAGE 44 | 92% | BRAIN SURGERY |
| ELLE | 12/12/2020 | IMAGE 5 | IMAGE 55 | 96% | BRAIN SURGERY |

FIG. 2B

APPARATUS, SYSTEM, AND METHOD FOR IMPLANTING SURGICAL MATERIAL

CROSS REFERENCE TO RELATED APPLICATIONS

This application is a continuation of, and claims the benefit of, U.S. patent application Ser. No. 17/723,404, filed Apr. 18, 2022, the disclosure of which is hereby incorporated, in its entirety, by this reference.

BACKGROUND

The present disclosure is generally related to an apparatus, a system, and a method for implanting surgical material.

Various surgeries involve cell/tumor removal and/or inserting an implant inside a patient's body, during a surgical procedure. One such type of tumor is glioma, a type of tumor that starts in the glial cells of the brain or the spine. Further, gliomas comprise about 30 percent of all brain tumors and central nervous system tumors, and 80 percent of all malignant brain tumors. Gliomas can occur in the brain and in various locations in the nervous system, including the brain stem and spinal column. Different types of gliomas cause different symptoms. Some include headaches, seizures, irritability, vomiting, visual difficulties and weakness or numbness of the extremities. Treatments include surgery, radiation therapy, chemotherapy and targeted molecular therapy. Further, glioma is generally treated by using carmustine. Carmustine, in general, is used to treat certain types of brain tumors. Carmustine belongs to a class of drugs known as alkylating agents. It works by slowing or stopping the growth of cancer cells. Carmustine, is usually facilitated to the patient's body, in form of wafers. In particular, Gliadel wafers (made of carmustine and polifeprosan) are used for the treatment of patients with newly-diagnosed high-grade glioma as an adjunct to surgery and radiation.

Currently, the implant is customized with the help of scissors. As a result, use of scissors tend to create an imprecise implant and further is a time-consuming process. Further, the existing system do not carry out analysis of area of insertion of the implant and simultaneously lack in providing accurate dimensioning and creation of the implant.

Thus, a novel system is required that can overcome all the aforementioned limitations and provide a customized implant, during a surgery procedure.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a laser cutter network which may be a two-dimensional (2d) laser cutter network. The system also includes a laser cutter which may be a 2D or 3-dimensional (3D) laser cutter; and a processor configured with instructions that, when executed by the processor, cause the processor to perform the steps of: capturing, with an imaging device, an image of an open area of the patient's body; creating, based at least in part on the captured image, a customized implant substrate, placing the implant substrate in the open area of the patient's body; and sealing the open area, after placing the customized implant substrate in the open area. Other embodiments of this aspect include corresponding computer systems, apparatus, and computer programs recorded on one or more computer storage devices, each configured to perform the actions of the methods.

Implementations may include one or more of the following features. The implant substrate may be any suitable substrate and may include prosthetic substrate, rhinoplasty substrate, structural biologic substrate, biological material substrate, synthetic substrate, coated substrate (e.g., drug or antibiotic coated or impregnated substrate), or the like.

The system as described may include placing an XY scale adjacent the open area and where the image of the open area of the patient's body includes the XY scale. The XY scale is any type of scale that may include indicia or markings to show a relative size of the open area in comparison with the XY scale. The XY scale may show indicia in one dimension, in two dimensions, or in three dimensions to allow the system to determine the size of the open are and crate the drug implant substrate to be a suitable size and shape for the open area. Creating the drug implant substrate may include shaping the drug implant substrate using the 2d laser cutter. The instructions further cause the processor to determine an accuracy score for the customized drug implant substrate. The system as described may include determining that the accuracy score is above a threshold score. The system may include determining that the accuracy score is below a threshold score. The system may, based at least in part to determining that the accuracy score is below a threshold score, provide feedback that the accuracy score is below a threshold. The feedback may include an alert, a warning, a disposing of the customized drug implant substrate. The system may be configured to retrieve, via the network, a 2D cut profile. The network may allow the system to access a variety of 2D cut profiles and the system may select a 2D cut profile to retrieve. The instructions may further cause the processor to actuate the 2D laser cutter to shape the drug implant substrate according to the 2D cut profile. The instructions may further cause the processor to add one or more tabs to expand a size of the drug implant substrate and where creating the drug implant substrate may include cutting the drug implant substrate to include the one or more tabs. In other words, the one or more tabs increase the surface area of the drug implant substrate and extend the periphery. The instructions may further cause the processors to actuate the 2D laser cutter to remove the one or more tabs from the drug implant substrate. In some cases, the one or more tables are removed after the drug implant substrate has been applied to the open area in the patient. The instructions may further cause the processor to scale the image based at least in part on an XY scale displayed in the image. Implementations of the described techniques may include hardware, a method or process, or computer software on a computer-accessible medium.

According to some embodiments, a surgical method is provided which may include the steps of opening and cleaning an implant area within a patient; capturing, with an imaging device, an image of the implant area; creating, based at least in part on the image of the implant area, a 2D profile for an implant substrate; cutting, based at least in part on the 2D profile and with a 2D laser cutter, the implant substrate; positioning the implant substrate into the implant area within the patient; and closing the implant area within the patient. Other embodiments of this aspect include corresponding computer systems, apparatus, and computer programs recorded on one or more computer storage devices, each configured to perform the actions of the methods.

Some embodiments may include one or more of the following features. The surgical method may include the step of placing an XY scale adjacent the implant area prior to capturing the image of the implant area. The surgical method as may include the step of loading the implant substrate into the 2D laser cutter prior to cutting the implant substrate. The step of cutting the implant substrate may include cutting around the one or more tabs. The surgical method as may include the step of adding a solution to the implant substrate to create biocompatibility between the implant substrate and the patient. The surgical method as described may include the step of receiving, via a computer user interface, an input from a user of a computer system that guides the surgical method. The surgical method may include the step of establishing a communications link between the one or more processors and a 2D laser cutter network and retrieving, from the 2D laser cutter network a 2D cut profile. The surgical method may include the step of modifying the 2D cut profile, which may be done by the system, or by user input through a user interface. The surgical method may include the step of scaling the captured image to create a scaled image and cutting, with the 2D laser cutter, the implant substrate based at least in part on the scaled image. The surgical method as may include the step of capturing, with the imaging device, a second image that displays the implant substrate and the implant area. The surgical method as may include the step of determining an accuracy score between the implant substrate and the implant area and displaying the accuracy score on a user interface. The surgical method may include the step of determining that the accuracy score is below a threshold score and display an indicia of the accuracy score being below the threshold score. The surgical method may further include the step of cutting, based at least on the accuracy score, a subsequent implant substrate. For example, the system may learn why the implant substrate receive the accuracy score and adjust the cutting profile based on the first implant substrate cut profile to cut a subsequent implant substrate. Implementations of the described techniques may include hardware, a method or process, or computer software on a computer-accessible medium.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles. Certain embodiments of the disclosure are described more fully below with reference to the accompanying drawings. However, various aspects of the disclosure may be implemented in many different forms and should not be construed as being limited to the implementations set forth herein. Like numbers refer to like, but not necessarily the same or identical, elements throughout.

FIG. 2A illustrates a $3^{rd}$ party 2D laser shape database, according to an embodiment;

FIG. 2B illustrates a local database, according to some embodiments;

DETAILED DESCRIPTION

Figure 1:
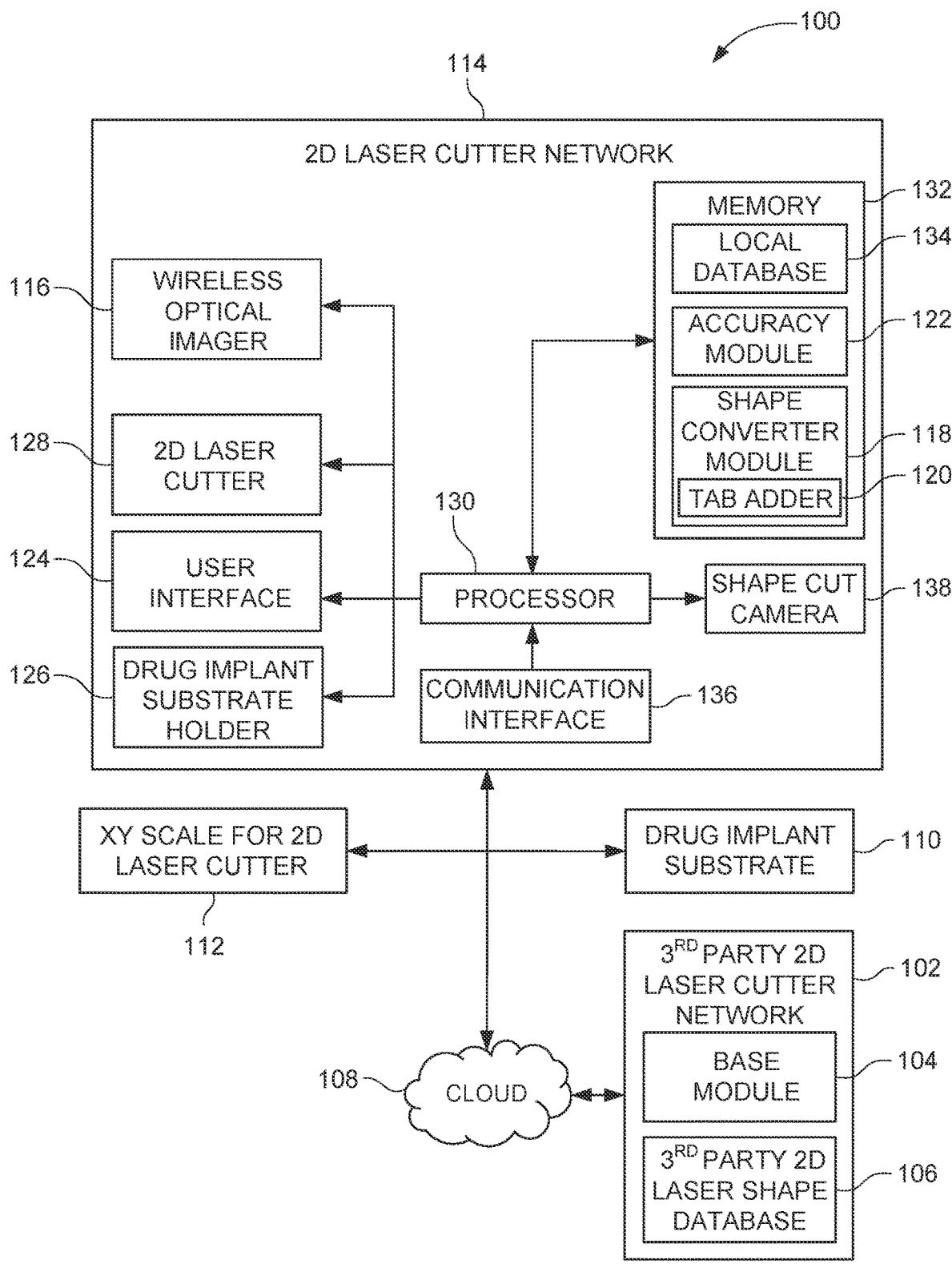
FIG. 1 illustrates a block diagram of a system for customizing an implant, according to some embodiments.

Some embodiments of this disclosure, illustrating at least some of its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Advanced surgical systems include many different types of equipment to monitor and anesthetize the patient, assist the surgeon in performing surgical tasks, and maintain the environment of the operating room. Non-limiting examples of surgical equipment that may be used or improved by the present invention are provided for reference.

Vital signs monitor refers to medical diagnostic instruments and in particular to a portable, battery powered, multi-parametric, vital signs monitoring device that can be used for both ambulatory and transport applications as well as bedside monitoring. These devices can be used with an isolated data link to an interconnected portable computer allowing snapshot and trended data from the monitoring device to be printed automatically and also allowing default configuration settings to be downloaded to the monitoring device. The monitoring device is capable of use as a standalone unit as well as part of a bi-directional wireless communications network that includes at least one remote monitoring station. A number of vital signs monitoring devices are known that are capable of measuring multiple physiologic parameters of a patient wherein various sensor output signals are transmitted either wirelessly or by means of a wired connection to at least one remote site, such as a central monitoring station. A vital signs monitor can be integrated into some embodiments in a variety of manners.

Heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc. A heart rate monitor can be integrated into some embodiments in a variety of manners.

Pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. A pulse oximeter can be integrated into some embodiments in a variety of manners.

End Tidal CO2 monitor or capnography monitor refers to an instrument which is used for measurement of level of carbon dioxide (referred to as end tidal carbon dioxide, ETCO2) that is released at the end of an exhaled breath. End Tidal CO2 monitor or capnography monitor is widely used in anesthesia and intensive care. ETCO2 can be calculated by plotting expiratory CO2 with time. Further, ETCO2 monitor plays a very crucial role for the measurement of applications such as Cardiopulmonary Resuscitation (CPR), Airway assessment, Procedural sedation and analgesia, Pulmonary diseases such as obstructive pulmonary disease, pulmonary embolism, etc., heart failure, metabolic disorders, etc. The instrument can be configured as side stream (diverting) or mainstream (non-diverting). Diverting device transports, a portion of a patient's respired gases from the sampling site to the sensor while non-diverting device does not transport gas away. Also, measurement by the instrument is based on the absorption of infrared light by carbon dioxide; where exhaled gas passes through a sampling chamber containing an infrared light source and photodetector on both sides. Based on the amount of infrared light reaching the photodetector, the amount of carbon dioxide present in the gas can be calculated. An ETCO2 monitor or capnography monitor can be integrated into some embodiments in a variety of manners.

Blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (i.e., systolic blood pressure, occurs when heart beats and pushes blood through the arteries) and ventricular diastole (i.e., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. The cuff then inflates until it fits tightly around your arm, cutting off your blood flow, and then the valve opens to deflate it. It operates by inflating a cuff tightly around the arm, as the cuff reaches the systolic pressure, blood begins to flow around your artery, and creating a vibration which is detected by the meter, which records your systolic pressure. This systolic pressure is recorded. The techniques used for measurement may be: auscultatory or oscillometric. A blood pressure monitor can be integrated into some embodiments in a variety of manners.

Body temperature monitor refers to any instrument which is used for measurement of body temperature. The instrument can measure the temperature invasively or non-invasively by placement of sensor into organs such as bladder, rectum, esophagus, tympanum, esophagus, etc., and mouth, rectum, armpit, etc., respectively. The sensors are of two types: contact and non-contact. It can be measured in two forms: core temperature and peripheral temperature. Temperature measurement can be done by these sensing technologies: thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. A blood temperature monitor can be integrated into some embodiments in a variety of manners.

Respiration rate or breathing rate is the rate at which breathing occurs and is measured by a number of breaths a person takes per minute. The rate is usually measured when a person is at rest and simply involves counting the number of breaths for one minute by counting how many times the chest rises. Normal respiration rates for an adult person at rest are in the range: 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. Respiratory rate can be integrated into some embodiments in a variety of manners.

An electrocardiogram abbreviated as EKG or ECG refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, and cardiomyopathy, among others. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. An electrocardiogram can be integrated into some embodiments in a variety of manners.

Neuromonitoring also called Intraoperative neurophysiological monitoring (abbreviated as IONM) refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), Somatosensory Evoked Potential (SSEP), transcranial electrical motor evoked potentials (TCeMEP), Electromyography (EMG), electroencephalography (EEG), and auditory brainstem response (ABR). The use of neurophysiological monitoring during surgical procedures requires specific anesthesia techniques to avoid interference and signal alteration due to anesthesia. Neuromonitoring can be integrated into some embodiments in a variety of manners.

Motor Evoked Potential abbreviated as MEP refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. MEP can be integrated into some embodiments in a variety of manners.

Somatosensory evoked potential abbreviated as SSEP or SEP refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality. Somatosensory evoked potential can be integrated into some embodiments in a variety of manners.

Electromyography abbreviated as EMG refers to the evaluation and recording of electrical signals or electrical activity of the skeletal muscles. Electromyography instrument or Electromyograph or Electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. Electromyography can be integrated into some embodiments in a variety of manners.

Electroencephalography abbreviated as EEG refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are Alpha, Beta, Theta, and Delta. Electroencephalography can be integrated into some embodiments in a variety of manners.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, ultrasound, X-rays, computed tomography, magnetic resonance imaging, nuclear medicine imaging, positron emission tomography, arthrogram, myelogram, mammography, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. Medical visualization systems can be integrated into some embodiments in a variety of manners.

A microscope refers to an instrument that is used for viewing samples and objects that cannot be seen with an unaided eye. A microscope may have components eyepiece, objective lenses, adjustment knobs, stage, illuminator, condenser, diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. A microscope may be of types compound (light illuminated and the image seen with the microscope is two dimensional), dissection or stereoscope (light illuminated and image seen with the microscope is three dimensional), confocal (laser-illuminated and image seen with the microscope on a digital computer screen), Scanning Electron abbreviated as SEM (electron illuminated and image seen with the microscope in black and white), Transmission Electron Microscope abbreviated as TEM (electron illuminated and image seen with the microscope is the high magnification and high resolution). A microscope can be integrated into some embodiments in a variety of manners.

Endoscopes or arthroscopes or laparoscopes refer to minimally invasive surgical techniques where procedures are performed by performing minimal incision in the body. An Endoscope refers to an instrument to visualize, diagnose, and treat problems inside hollow organs where the instrument is inserted through natural body openings such as the mouth or anus. An endoscope may perform a procedure as follows: scope with a tiny camera attached to a long, thin tube is inserted. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and perform procedures on cartilage, ligaments, tendons, etc. An endoscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Endoscope refers to an instrument to visualize, diagnose, and treat problems inside soft organs like the abdomen and pelvis by a TV camera inserted through small portals/incisions and perform procedures. Endoscopes/arthroscopes/laparoscopes or minimally invasive surgery techniques can be integrated into some embodiments in a variety of manners.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optics sensors comprise a light source, optical fiber, external transducer, and photodetector. Fiber-optic sensors may be intrinsic or extrinsic. Fiber optics sensors may be categorized into four types physical, imaging, chemical, and biological. Fiber optics can be integrated into some embodiments in a variety of manners.

Ultrasound refers to using sound waves to produce images of the inside of a body. In many cases, an ultrasound may be used by placing a small probe on the skin of a patient. In some cases, an ultrasound may be inserted into natural body openings, such as the anus in the case of a transrectal ultrasound probe (TRUS). The ultrasound emits high-frequency sound waves into the body. In some cases, a gel is placed on the skin to facilitate sound transmission and movement of the ultrasound. A computing device may be connected to the probe and receives sound waves that are reflected off of body tissues and creates an image. Ultrasound can be integrated into some embodiments in a variety of manners.

X-ray refers to radiography using x-ray radiation to produce a picture of the targeted body part below the skin. It may often be used to visualize and diagnose bone ailments, infections, injury, or locating foreign objects. X-ray may be integrated into some embodiments in a variety of manners.

Computed tomography (CT scan) refers to a combination of X-ray images taken from multiple angles. The plurality of X-ray images may be combined by a computing device to generate cross-sectional images of the bones, blood vessels, and soft tissues. A CT scan may be used for diagnostic purposes. CT scan may be integrated into some embodiments in a variety of manners.

Magnetic resonance imaging (MRI) refers to applying a magnetic field, such as through radio waves, and a computing device to receive the reflected magnetic field to produce images of organs and tissues. MRI may be integrated into some embodiments in a variety of manners.

Nuclear medicine imaging refers to producing images by detecting radiation from different parts of the body after a radioactive tracer material is administered, which may be intravenously, orally, or otherwise. Nuclear medicine imaging may be integrated into some embodiments in a variety of manners.

Positron emission tomography refers to an imaging technique that uses radioactive substances such as radiotracers to visualize and measure changes in metabolic processes and in other physiological activities including blood flow, regional chemical composition, and absorption, among others. Positron emission tomography may be integrated into some embodiments in a variety of manners.

Arthrogram refers to a diagnostic imaging procedure that uses X-rays to guide and evaluate the injection and/or flow paths of contrast medial directly into a joint. It may used as procedure to supplement imaging data obtained through an MRI or CT scan. Arthrogram may be integrated into some embodiments in a variety of manners.

Myelogram refers to injecting a special dye and X-ray imaging to capture images of the special dye. It can be used to obtain imaging data of the bones and fluid-filled spaces between the bones. In many cases, a myelogram is performed in conjunction with a CT scan to take advantage of the dye injected into the body. A myelogram may be integrated into some embodiments in a variety of manners.

Mammography refers to using low energy X-rays to examine breast tissue, such as for early detection of breast cancer. It may be used for diagnostic purposes and may be used to render 3D images to detect tumors. Mammography may be integrated into some embodiments in a variety of manners.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. Surgical lights can be integrated into some embodiments in a variety of manners.

High-definition monitors refer to a display in which a clearer picture than possible with low-definition, low-resolution screens. High-definition monitors have a higher density of pixels per inch than past standard TV screens. Resolution for high-definition monitors may be 1280×720 pixels or more. Full HD—1920×1080, Quad HD—2560×1440, 4K—3840×2160, 8K—7680×4320 pixels. High-definition monitor may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, etc.), better visualization of blood vessels and lesions. High-definition monitors can be integrated into some embodiments in a variety of manners.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for this purpose: educational purposes: example—to broadcast a live feed of a surgical demonstration to a remote audience, to collect authentic footage for edited, instructional videos on a surgical technique or procedure; to facilitate video enhanced debriefing and coaching, or to formally assess surgical skills. Operating room cameras can be integrated into some embodiments in a variety of manners.

Surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery, abbreviated as MIS. MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, joint, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, fluid jet, sensors, etc. A surgical tower can be integrated into some embodiments in a variety of manners.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example: after removing part of the liver for removal of tumor etc., blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in modes two monopolar or bipolar. The electrocautery instrument may consist of a generator, a handpiece, and one or more electrodes. Electrocautery can be integrated into some embodiments in a variety of manners.

Radiofrequency (RF) is used in association with minimally invasive surgery devices. The radiofrequency (RF) may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs. The RF may be used to perform an endoscopic surgery on the body such as the spine by delivery of RF energy. Radiofrequency can be integrated into some embodiments in a variety of manners.

Laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastrointestinal tract, eye, nose, and throat. Lasers are used in minimally invasive surgery to ablate soft tissues, such as a herniated spinal disc bulge. Laser can be integrated into the embodiments in a variety of manners.

Fluid jet involves using a high-pressure fluid stream, such as liquid (e.g., water) or gas, aimed at tissue. The liquid pressure may impinge on the targeted tissue and may be used to cut, incise, perforate, and/or ablate the target tissue. In some cases, the liquid jet creates cavitations that may be used to ablate a volume of tissue. Liquid jet may be integrated into some embodiments in a variety of manners.

Sensors are used in association with minimally invasive surgery devices. The sensor may be used in minimally invasive surgeries for tactile sensing of tool—tissue interaction forces. During minimally invasive surgeries field of view and workspace of tools are compromised due to the indirect access to the anatomy and lack of surgeon's hand-eye coordination. The sensors provide a tactile sensation to the surgeon by providing information of shape, stiffness, and texture of organ or tissue (different characteristics) to surgeon's hands through a sense of touch. This detection of a tumor through palpation, which exhibit a 'tougher' feel than healthy soft tissue, pulse felt from blood vessels, and abnormal lesions. The sensors may provide in output shape, size, pressure, softness, composition, temperature, vibration, shear, and normal forces. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. Sensors can be integrated into some embodiments in a variety of manners.

Imaging systems refer to techniques or instruments which are used for the creation of images and visualization of the interior of a human body for diagnostic and treatment purposes. Imaging systems play a crucial role in every medical setting and can help in the screening of health conditions, diagnosing causes of symptoms, monitor health conditions. Imaging systems may include various imaging techniques such as X-ray, Fluoroscopy, Magnetic resonance imaging (MRI), Ultrasound, Endoscopy, Elastography, Tactile imaging, Thermography, Medical photography, and Nuclear medicine e.g., Positron emission tomography (PET). Some factors which may drive the market are cost and clinical advantages of medical imaging modalities, a rising share of ageing populations, increasing prevalence of cardiovascular or lifestyle diseases, increasing demand from emerging economies. Some factors which may inhibit the market are saturation in many segments, high costs, lack of trained personnel. Imaging systems can be integrated into some embodiments in a variety of manners.

X-ray refers to a medical imaging instrument that uses X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, etc. An X-ray can be integrated into some embodiments in a variety of manners.

Magnetic resonance imaging abbreviated as MRI refers to a medical imaging instrument that uses powerful magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field, and energy release is dependent on environmental factors and the chemical nature of the molecules. MRI may more widely suit for imaging of non-bony parts or soft tissues of the body. MRI may be less harmful as it does not use damaging ionizing radiation as in the X-ray instrument. MRI instrument may consist of magnets, gradients, radiofrequency system, computer control system. Some areas where imaging by MRI should be prohibited may be people with implants. Mill can be integrated into some embodiments in a variety of manners.

Computed tomography imaging abbreviated as CT refers to a medical imaging instrument that uses an X-ray radiation (i.e., X-ray range in the electromagnetic radiation spectrum) for the creation of cross-sectional images of the interior of the human body for diagnostic and treatment purposes. CT refers to a computerized x-ray imaging procedure in which a narrow beam of x-rays is aimed at a patient and quickly rotated around the body, producing signals that are processed by the machine's computer to generate cross-sectional images—or "slices"—of the body The CT instrument produces cross-sectional images of the body. Computed tomography instrument is different from an X-ray instrument as it creates 3-dimensional cross-sectional images of the body while X-ray creates 2-dimensional images of the body; the 3-dimensional cross-sectional images are created by taking images from different angles, which is done by taking a series of tomographic images from different angles. The different taken images are collected by a computer and digitally stacked to form a three-dimensional image of the patient. For creation of images by the CT instrument, a CT scanner uses a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. CT can be integrated into some embodiments in a variety of manners.

Stereotactic navigation systems refer to an instrument that uses patient imaging (e.g., CT, MRI) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. Stereotactic navigation systems can be integrated into some embodiments in a variety of manners.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, etc., in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. Ultrasound can be integrated into some embodiments in a variety of manners.

Anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machine may perform following functions provides O2, accurately mix anesthetic gases and vapors, enable patient ventilation, and minimize anesthesia related risks to patients and staff. Anesthesia machine may consist of the following essential components a source of oxygen (O2), O2 flowmeter, vaporizer (anesthetics include isoflurane, halothane, enflurane, desflurane, sevoflurane, and methoxyflurane), patient breathing circuit (tubing, connectors, and valves), scavenging system (removes any excess anesthetics gases). Anesthesia machine may be divided into three parts the high pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. An anesthesiology machine can be integrated into some embodiments in a variety of manners.

Surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation Bed, fracture bed. Some essential components of a surgical bed may be bed sheet, woolen blanket, bath towel, bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, prepared to meet any emergency. Surgical bed can be integrated into some embodiments in a variety of manners.

Disposable air warmer (also referred to as bair) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. Disposable air warmer can be integrated into some embodiments in a variety of manners.

Sequential compression device abbreviated as SVD refers to an instrument that is used to help prevent blood clots in the deep veins of legs. The sequential compression device use cuffs around the legs that fill with air and squeeze your legs. This increases blood flow through the veins of your legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. Sequential compression device can be integrated into some embodiments in a variety of manners.

Jackson frame refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. The Jackson frame can be integrated into some embodiments in a variety of manners.

Bed position controller refers to an instrument for controlling the position of the patient bed. Positioning a patient in bed is important for maintaining alignment and for preventing bed-sores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, Trendelenburg position. Bed position controller can be integrated into some embodiments in a variety of manners.

Operating room environmental controls refers to control or maintenance of the environment in an operation theatre where procedures are performed to minimize the risk of airborne infection and provide a conducive environment for everyone in the operation theatre-surgeon, anesthesiologist, nurses & patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors environmental humidity, infection, odor control. Humidity control may be done by controlling the temperature of anesthesia gases; Infection can be controlled by the use of filters to purify the air. Operating room environmental controls can be integrated into some embodiments in a variety of manners.

Heating, ventilation, and air conditioning (abbreviated as HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. Heating, ventilation, and air conditioning can be integrated into some embodiments in a variety of manners.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, etc., to remove all infectious particles down and away from the patient. Air purification system may be air curtain, multi-diffuser array, or single large diffuser (based on laminar diffuser flow) or High-Efficiency Particulate Air filter. High-Efficiency Particulate Air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. Air purification can be integrated into some embodiments in a variety of manners.

Orthopedic tools also referred to as orthopedic instruments used for treatment and prevention of deformities and injuries of musculoskeletal system or skeleton, articulations, and locomotive system (i.e., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, etc. Orthopedic tools can be integrated into some embodiments in a variety of manners.

Drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks harm caused to bone, muscle, nerves, and venous tissues are wrapped by surrounding tissue, the drill does not stop immediately. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, cooling systems. The drill may consist of components physical drill, cord power, electronically motorized bone drill, rotating bone shearing incision work unit. Drill can be integrated into some embodiments in a variety of manners.

Scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. Scalpel can be integrated into some embodiments in a variety of manners.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of type based on coating coated and un-coated. Stitches can be integrated into some embodiments in a variety of manners.

Stapler refers to a tool for fragment fixation when interfragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Stapler may be made of surgical grade stainless steel or titanium and they are thicker, stronger, and larger. The stapler can be integrated into some embodiments in a variety of manners.

Equipment refers to a set of articles, tools, or objects which help to implement or achieve an operation or activity. A medical equipment refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, etc. The medical equipment works by taking a signal from a measurand/patient, a transducer for converting one form of energy to electrical energy, signal conditioner such as an amplifier, filters, etc., to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. A medical equipment can be integrated into some embodiments in a variety of manners.

Ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, etc. A ventilator may be operated in modes ACV, SIMV, PCV, PSV, PCIRV, APRV, etc. A ventilator may have components gas delivery system, power source, control system, safety feature, gas filter, monitor. A ventilator can be integrated into some embodiments in a variety of manners.

Continuous positive airway pressure abbreviated as CPAP refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps the patient with sleep apnea to breathe more easily during sleep by sending a steady flow of oxygen into the nose and mouth during sleep, which keeps the airways open and helps to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, adjustable straps. The essential components may be a motor, a cushioned mask, a tube that connects the motor to the mask. Continuous positive airway pressure instruments can be integrated into some embodiments in a variety of manners.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are time-saving, no risk of healthcare-associated infections, cost-efficient) or sterilizable (cross-contamination, risk of surgical site infections, sterilization). Consumables can be integrated into some embodiments in a variety of manners.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, etc. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into Surgical Robotic Systems, Rehabilitative Robotic Systems, Non-invasive Radiosurgery Robots, Hospital & Pharmacy Robotic Systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally-invasive procedures. The systems comprise computer-controlled electromechanical devices that work in response to controls manipulated by the surgeons. Robotic systems can be integrated into some embodiments in a variety of manners.

An Electronic Health Record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, etc. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. The EHR can be integrated into some embodiments in a variety of manners.

Equipment tracking systems, such as RFID, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including Radio-frequency Identification (RFID), Global Positioning System (GPS), Bluetooth Low Energy (BLE), barcodes, Near-Field Communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. Equipment tracking systems, RFID can be integrated into some embodiments in a variety of manners.

Quantum computing refers to any computational device or method which utilizes properties of quantum states defined by quantum mechanics such as superposition, entanglement, etc. to perform computations. These devices utilize qubits which are the quantum equivalent to bits in a classical computing system, comprised of at least two quantum states or probable outcomes. These outcomes, combined with a coefficient representing the probability of each outcome, describes the possible states, or bits of data, which can be represented by the qubits according to the principle of quantum superposition. These states may be manipulated which may shift the probability of each outcome or additionally add additional possible outcomes to perform a calculation, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that nature of quantum computing is the same as the systems being simulated. In medical fields, quantum computing shows the greatest promise for drug discovery and simulating the interaction of drugs with biologic systems, however the same technology might be used to predict the interaction of a biologic system with an implanted device, preventing rejection of an implant by a patient's body, long term function of an implant, and potentially the reaction of a patient to a surgical procedure during a simulation before a procedure or actively during a procedure. Quantum computing can be used with one or more embodiments in a variety of manners.

Embodiments of the present disclosure will be described more fully hereinafter with reference to the accompanying drawings in which like numerals represent like elements throughout the several figures, and in which example embodiments are shown. Embodiments of the claims my, however, be embodied in many different forms and should not be construed as limited to the specified embodiments shown and described herein. The examples set forth herein are non-limiting examples and are merely examples among other possible examples.

FIG. 1 illustrates a block diagram of a system 100 for implanting surgical material in a patient's body. The system may comprise a $3^{rd}$ party 2-dimensional (2D) laser cutter network 102, having a base module 104 and a $3^{rd}$ party 2D laser shape database 106 (described more fully in FIG. 2A). Further, the $3^{rd}$ party 2D laser cutter network 102 may be coupled, such as via a cloud network 108, to a 2-dimensional (2D) laser cutter 112. In one embodiment, the $3^{rd}$ party 2D laser cutter network 102 may be available at the site of surgical procedure (inside the operation room). While the illustrated embodiment shows and describes a 2D laser cutter network, it should be appreciated that a laser cutter network and laser cutter could be three-dimensions (3D). In other words, the laser cutter network can include 3D shapes, profiles, surfaces, or contours and the laser cutter may be capable of forming any suitable 3D shape.

In some embodiments, an additive manufacturing system may be incorporated to create a suitable substrate. For example, in some cases, a 3D printer may be used with embodiments disclosed herein, such as to create a substrate, modify a substrate, or provide a substrate blank that may later be further shaped by a laser cutter.

Any suitable 3D printer and printing technique may be employed to produce effective substrates as described herein. For instance, a substrate may be created through a suitable 3D printing technique and the substrate may subsequently be cut by a laser cutter as described herein. The substrates may include or be formed of biological material, synthetic material, a combination of biological and synthetic materials, contain a drug or antibiotic which may be coated and/or impregnated. In some examples a biological material may be used as a substrate which may be formed and shaped such as to close a heart defect. In this case, the substrate may be created as a perfectly shaped biological material which can be applied to an organ.

Further, the 3$^{rd}$ party 2D laser cutter network 102 may be coupled to a 2D laser cutter network 114, via the cloud network 108. The 2D laser cutter network 114 may comprise a wireless optical imager 116, a user interface 124, a drug implant substrate holder 126, a 2D laser cutter 128, one or more processors 130, a communication interface 136, and a shape cut camera 138. Further, the processor(s) 130 may be connected to one or more of a memory 132 having a local database 134 (described more fully in FIG. 2B), a shape converter module 118, optionally including a tab adder 120, and an accuracy module 122.

According to some example embodiments, the systems and/or methods described herein may be under the control of one or more processors. The one or more processors may have access to computer-readable storage media ("CRSM"), which may be any available physical media accessible by the processor(s) to execute instruction stored on the CRSM. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other medium which can be used to store the desired information and which can be accessed by the processor(s).

In one embodiment, the 3$^{rd}$ party 2D laser cutter network 102 may be associated with a manufacturer of the 2D laser cutter 128. Further, the 3$^{rd}$ party 2D laser cutter network 102 may be configured to facilitate a surgeon with function for customizing the shape of an implantable surgical material, using the base module 104, described below. It can be noted that the base module 104 may interact with the 2D laser cutter 128 in the system 100. Further, the base module 104 may use data from the 3$^{rd}$ party 2D laser shape database 106, described in conjunction with FIG. 2A. It can be noted that the 3$^{rd}$ party 2D laser shape database 106 may be used to store each operation or surgical procedure, which may include saving the shape identified and cut by the 2D laser cutter 128. In addition, the 3$^{rd}$ party 2D laser shape database 106 may be used to store each image of the patient or the surgical opening, for reference in future procedures. In some cases, a surgeon may specify a unique shape, or modify a shape in the 2D laser shape database 106 for use by the surgeon. A unique shape and/or a modified shape may be stored in the 2D laser shape database 106 or may be stored in the local database 134 for later use.

The 3$^{rd}$ party 2D laser shape database 106, as described more fully in, and with reference to, FIG. 2A, may store one or more of a patient's name, date of surgical procedure, shape identified for surgical opening, image of surgical opening, and an accuracy score. For example, for patient Alex, with surgical procedure performed on 20/11/2020, with a shape identified for surgical opening as per Image 1, an image of surgical opening as Image 21, and an accuracy score of 96% may be determined based on the cut out shape fills the surgical opening. Further, for patient Barrie, with surgical procedure performed on 18/9/2020, with a shape identified for surgical opening as per Image 2, an image of surgical opening as Image 22, and an accuracy score of 98%. Further, for patient Catherine, with surgical procedure performed on 6/7/2021, with a shape identified for surgical opening as per Image 3, an image of surgical opening as Image 33, and an accuracy score of 94%. Further, for patient Darwin, with surgical procedure performed on 19/2/2021, with a shape identified for surgical opening as per Image 4, an image of surgical opening as Image 44, and an accuracy score of 92%. Further, for patient Elle, with surgical procedure performed on 12/12/2020, with a shape identified for surgical opening as per Image 5, an image of surgical opening as Image 55, and an accuracy score of 96%. It can be noted that the image of surgical opening may include the size and dimensions of the surgical opening.

It can be noted that in some cases the cloud network 108 may facilitate communication between the 3$^{rd}$ party 2D laser cutter network 102 and the 2D laser cutter network 114. In some embodiments, the cloud network 108 to be implemented using a collection of server devices to provide one or more services to coupled devices and data sources. Further, the cloud network 108 may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques, as may be now known, or future developed, in the communication arts.

In some embodiments, a drug implant substrate 110 may act as a replacement of wafers used in a surgical procedure (for example, a Gliadel wafer used for brain surgery). Further, the drug implant substrate 110 may be rectangular in shape and may be available in varying sizes and have a pre-defined dosing per square inch, without departing from the scope of the disclosure. It can be noted that the drug implant substrate 110 may comprise multiple layers of substrate and may include layers of additional materials used for packing and closing the opening for implant. Further, the drug implant substrate 110 may be provided as a stack of layers which may be cut and placed as one unit. It can be noted that such use of the drug implant substrate 110 may facilitate reduced amount of packaging. Further, the XY scale for 2D laser cutter 112 may be a ruler for reference when imaging opening for implant, to provide scale. It can be noted that the XY scale for 2D laser cutter 112 may be working in conjunction with the wireless optical imager 116 and the shape cut camera 138. In some embodiments, the XY scale for 2D laser cutter 112 may comprise an additional means for capturing curvature. For instance, one or more cameras that may use visible, infrared, or ultraviolet light may be used to determine curvature of a cutting surface. In some cases, a plurality of lasers may be used to map a curvature of a cutting surface and the one or more processors may determine the cut profile and depth based at least in part on the curvature of the cutting surface.

In some embodiments, the 2D laser cutter network 114 may correspond to a network present at the site of the surgical procedure. Further, the 2D laser cutter 128 may be a commercially available laser cutter and may be adapted for use in the operating room. Further, the 2D laser cutter network 114 may comprise the wireless optical imager 116. In some embodiments, the wireless optical imager 116 may be wireless or wired. Further, the wireless optical imager 116 may be used to capture images of a surgical opening for inserting the implant in the patient's body. In some embodiments, the wireless optical imager 116 may be coupled to the 2D laser cutter 128, may be integrated with the 2D laser cuter 128, or may be a discrete component, without departing from the scope of the disclosure. Further, the wireless optical imager 116 may be a camera or an image capturing apparatus which is compatible with the 2D laser cutter network 114.

Figure 3:
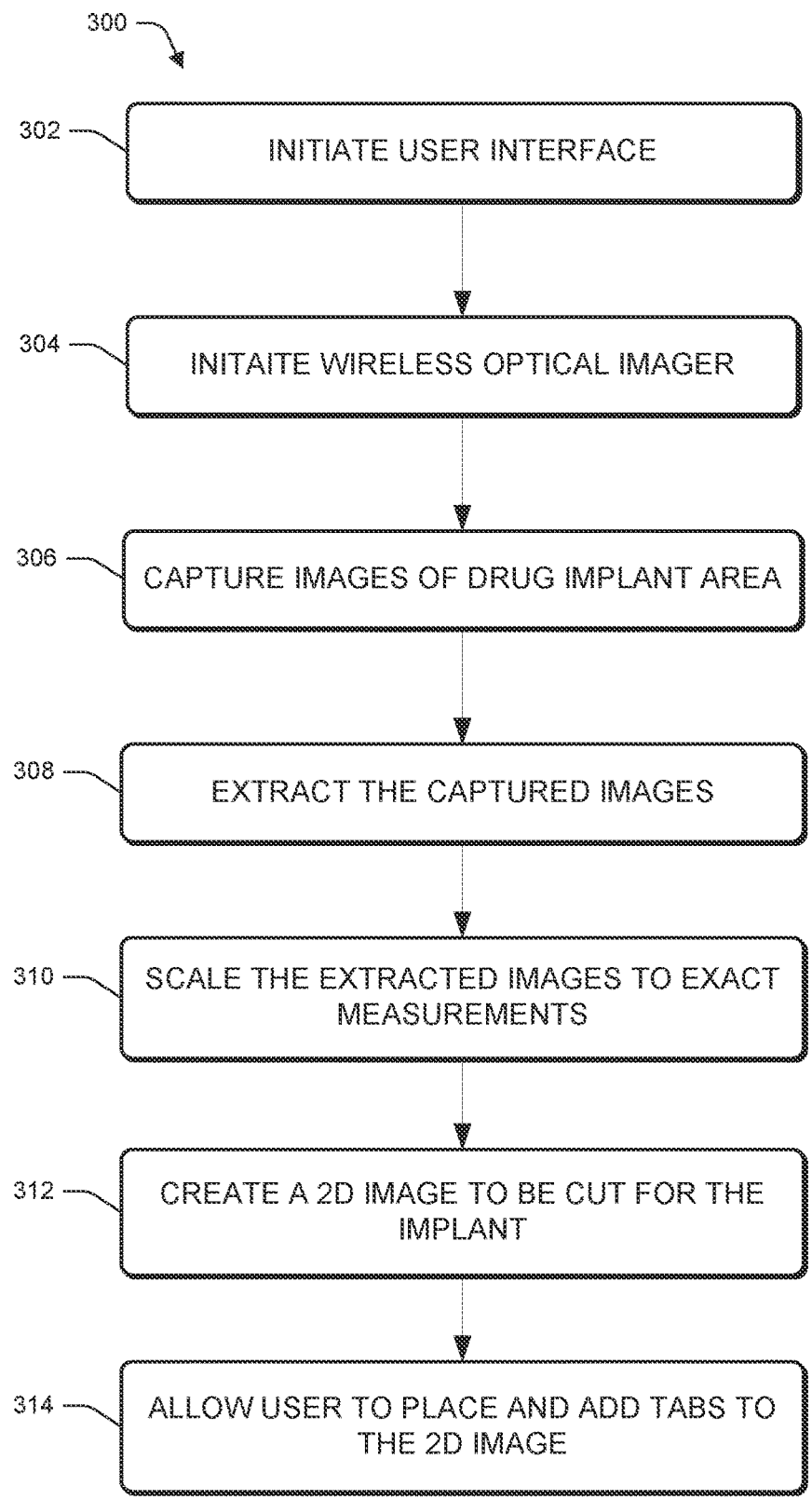
FIG. 3 illustrates a method for operation of a shape converter module, according to some embodiments.

Further, the 2D laser cutter network 114 may comprise the shape converter module 118. It can be noted that the shape converter module 118 may receive images from the wireless optical imager 116 and create a 2D image to be cut out. Further, the shape converter module 118 may identify edges of opening and account for any curvature to ensure correct dimension and amount of material may be included in the 2D shape. Further, the shape converter module 118 may comprise the tab adder 120. The tab adder 120 may be used to add small tabs around the shape formed by the shape converter module 118, such as to aid positioning of the implant, which may be removed at a later stage, such as with the help of scissors. It can be noted that the operation of the shape converter module 118 may be further described in conjunction with FIG. 3, which illustrates a flowchart showing a method 300 followed during the surgical procedure. FIG. 3 is explained in conjunction with FIG. 1. It should also be noted that in some alternative implementations, the functions noted in the blocks may occur out of the order noted in the drawings. For example, two blocks shown in succession in FIG. 3 may be executed substantially concurrently or the blocks may sometimes be executed in the reverse order, depending upon the functionality involved. In addition, the process descriptions or blocks in flow charts should be understood as representing decisions made by a hardware structure such as a state machine.

With additional reference to FIG. 3, the shape converter module 118 may initiate the user interface 124, at step 302. It can be noted that the user interface 124 may provide a selectable menu of features to the surgeon, for capturing images of the open area for inserting the drug implant substrate 110 in the patient's body. For example, the shape converter module 118 initiates the user interface 124 for Dr. Van to select an imaging area around the front portion of brain of patient Alex.

Further, the shape converter module 118 may initiate the wireless optical imager 116, at step 304. The shape converter module 118 may initiate the wireless optical imager 116 for capturing images related to the patient's body for performing the surgical procedure. The wireless optical imager 116 may capture the images for the open area of the patient's body. Further, the shape converter module 118 may capture images of the drug implant area, at step 306. It can be noted that the shape converter module 118 may capture images of the drug implant area, using the wireless optical imager 116, open to receive the drug implant substrate 110. For example, the shape converter module 118 captures an image—Image 21 of a front area of the brain of patient Alex, for implanting the drug implant substrate 110.

Further, the shape converter module 118 may extract the captured images, at step 308. The shape converter module 118 may extract the captured image from the wireless optical imager 116, via the cloud network 108. In one embodiment, the shape converter module 118 may facilitate edge detection, identify the boundaries of the opening and create a shape profile. It can be noted that the created shape may accommodate a curvature. For example, the shape converter module 118 extracts image 21 related to the front area of brain of patient Alex.

Further, the shape converter module 118 may scale the extracted images to desired measurements, at step 310. It can be noted that the extracted image may not be properly scaled for the measurements of the drug implant substrate 110 for the patient. Thus, it may be necessary to properly scale the images for the patient. It can be noted that the shape converter module 118 may have information related to the patient and the drug implant substrate 110, and thus scale the extracted images to exact measurements. It can be noted that the shape converter module 118 may use the XY scale for the 2D laser cutter 112 placed in or around the opening to ensure dimensions are properly scaled. Further, scaling the image may adjust the dimensions to account for curvature of the surface around the opening as appropriate. For example, the shape converter module 118 scales the image 21 having a width of 4 inches and a height of 3 inches, for patient Alex, to match the width and height of the implant site of the patient Alex.

Further, the shape converter module 118 may create a 2D image to be cut for the drug implant substrate 110, at step 312. It can be noted that based on the scaled image, the shape converter module 118 may cut a 2D image of the drug implant substrate 110, for insertion into the open area of the patient. The 2D image may allow the cut shape to fit within the opening, which may be three dimensional. For example, the shape converter module 118 may create the 2D image of the scaled image 21, according to the front area of brain of patient Alex. Further, the shape converter module 118 may allow the user to place and add tabs to the 2D image, at step 314. It can be noted that the user may use the tab adder 120 to create or add tabs to the 2D image. In some cases, the tab adder 120 may automatically add appropriate sized and positioned tabs to the 2D image for cutting. The tabs may allow the surgeon to cut the tabs later for precise fitting of the drug implant substrate 110. For example, the shape converter module 118 adds tabs of 0.5 mm spaced every 2 inches on outer circumference of the image 21.

Further, the 2D laser cutter network 114 may comprise the accuracy module 122. The accuracy module 122 may be used to compare an original opening on the patient's body and the cut-out shape, provided by the shape converter module 118. The accuracy module 122 may ensure accuracy of the 2D laser cutter 128. It can be noted that the precision of the 2D laser cutter 128 may be reflected as a parameter for the accuracy module 122. Firstly, the accuracy module 122 may include the step of imaging the placed customized implant in the patient's body. For example, the accuracy module 122 images the customized implant placed on the front area of brain of patient Alex. Successively, the accuracy module 122 may compare the size of the implant to the opening and thus determine an accuracy score, based on the fit of the implant shape to the shape of the opening. For example, the accuracy module 122 determines an accuracy score of 94%, implying that 94% of the opening is covered and that there is a 6% overlap of the implant with surrounding tissues or a combination of overlap and missing material. Further, the accuracy module 122 may save a calculated accuracy score to the local database 134 or to the 3$^{rd}$ party 2D laser shape database 106. It can be noted that the accuracy score may be useful in future for selecting a particular type of 2D laser cutter 128.

Further, the 2D laser cutter network 114 may comprise the user interface 124, which may facilitate the surgeon to operate the 2D laser cutter 128. Further, the user interface 124 may allow the surgeon to interact with the shape converter module 118. Further, the user interface 124 may be used for displaying controls related to the surgical procedure. Further, the user interface 124 may comprise, but is not limited to, a display device such as a touch screen to display controls related to surgery, an audio device such as speakers to send and receive instructions related to components of the 2D laser and surgery, and a haptic device such as touch device to control the 2D laser cutter 128. In one embodiment, the user interface 124 may be configured to display images of the area captured by the wireless optical imager 116 when the surgery is started. It can be noted that the user interface 124 may facilitate a method for of viewing progress. In some embodiments, the audio devices may include speakers and microphones for interacting with the 2D laser cutter 128. In some embodiments, the user interface 124 may include imaging device outputs and/or human computer interface devices, such as, without limitation, a touch screen, a mouse, a touch pad, a scroll wheel or ball, or other suitable human to computer interface devices. It can be noted that the user interface 124 may allow input of maximum allowable medication dose to ensure proper substrate is selected. Further, the user interface 124 may be used to input a maximum amount of heat which can be applied to the substrate.

Further, the 2D laser cutter network 114 may comprise the drug implant substrate holder 126 which may be configured to hold the drug implant substrate 110 in the 2D laser cutter to prevent movement which may tend to reduce its accuracy. Further, the 2D laser cutter network 114 may comprise the 2D laser cutter 128. The 2D laser cutter 128 may be any suitable cutting equipment without departing from the scope of the disclosure. Further, the 2D laser cutter 128 may be replaced with other forms of computer numerical control (CNC) cutter which may be using a rotating spindle, a knife, or any other cutting implement to cut out the 2D shaped required.

In some embodiments, the processor(s) 130 are configured to execute instructions that result in controlling functions of the 2D laser cutter network 114. Further, the processor(s) 130 may be configured to facilitate the operation of the 2D laser cutter 128 and the operation of the shape converter module 118. Further, the processor(s) 130 may be operated based on instructions stored in the memory 132. The memory 132 may comprise short-term volatile memory and/or long-term persistent memory. The memory 132 may comprise the local database 134. It can be noted that the local database 134 may store information related to the surgical procedures performed using the 2D laser cutter network 114. Further, the local database 134 may store information related to the surgical procedures performed using the 2D laser cutter 128. It can be noted that the local database 134 may be updated by the $3^{rd}$ party 2D laser shape database. The local database 134 may be stored in any suitable location, and may be accessible by the 2D laser cutter network 114 by a wired connection to a local storage device, or it may be accessed through a wireless connection, such as through the cloud network 108, or the internet.

The local database 134, as described in FIG. 2B may store patient's name, date of surgical procedure, shape identified for surgical opening, image of surgical opening, an accuracy score, and procedure performed. For example, for patient Alex, with surgical procedure performed on 20/11/2020, with a shape identified for surgical opening as per Image 1, an image of surgical opening as Image 21, and an accuracy score of 96% for a brain surgery. Further, for patient Barrie, with surgical procedure performed on 18/9/2020, with a shape identified for surgical opening as per Image 2, an image of surgical opening as Image 22, and an accuracy score of 98% for a brain surgery. Further, for patient Catherine, with surgical procedure performed on 6/7/2021, with a shape identified for surgical opening as per Image 3, an image of surgical opening as Image 33, and an accuracy score of 94% for a brain surgery. Further, for patient Darwin, with surgical procedure performed on 19/2/2021, with a shape identified for surgical opening as per Image 4, an image of surgical opening as Image 44, and an accuracy score of 92% for a brain surgery. Further, for patient Elle, with surgical procedure performed on 12/12/2020, with a shape identified for surgical opening as per Image 5, an image of surgical opening as Image 55, and an accuracy score of 96% for a brain surgery.

In some embodiments, the 2D laser cutter network 114 comprises the communication interface 136 communicatively coupled to the processor 130 and the memory 132. In one embodiment, the communication interface 136 may be configured to facilitate communication from the 2D laser cutter network 114 to the $3^{rd}$ party 2D laser cutter network 102 over the cloud network 108. In one embodiment, the communication interface 136 may be a radio communication or other wired or wireless communication. It can be noted that the communication interface 136 may communicate with the cloud network 108 to be implemented to provide one or more services to coupled devices and data sources. Further, the communication interface 136 may be a wired and/or a wireless network. The communication interface 136, if wireless, may be implemented using communication techniques such as, without limitation, Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques, known in the art or later developed.

Further, the shape cut camera 138 may be an image capturing apparatus and may be used to capture images of shape as being cut by the 2D laser cutter 128. Further, the shape cut camera 138 may ensure that the 2D laser cutter 128 is properly calibrated. Further, the shape cut camera 138 may allow for correction of errors on the fly or in real-time. Further, the shape cut camera 138 may image the opening for the insertion of the implant, after a shape has been placed to compare the shape to the opening, as performed by the shape converter module 118.

Figure 4A:
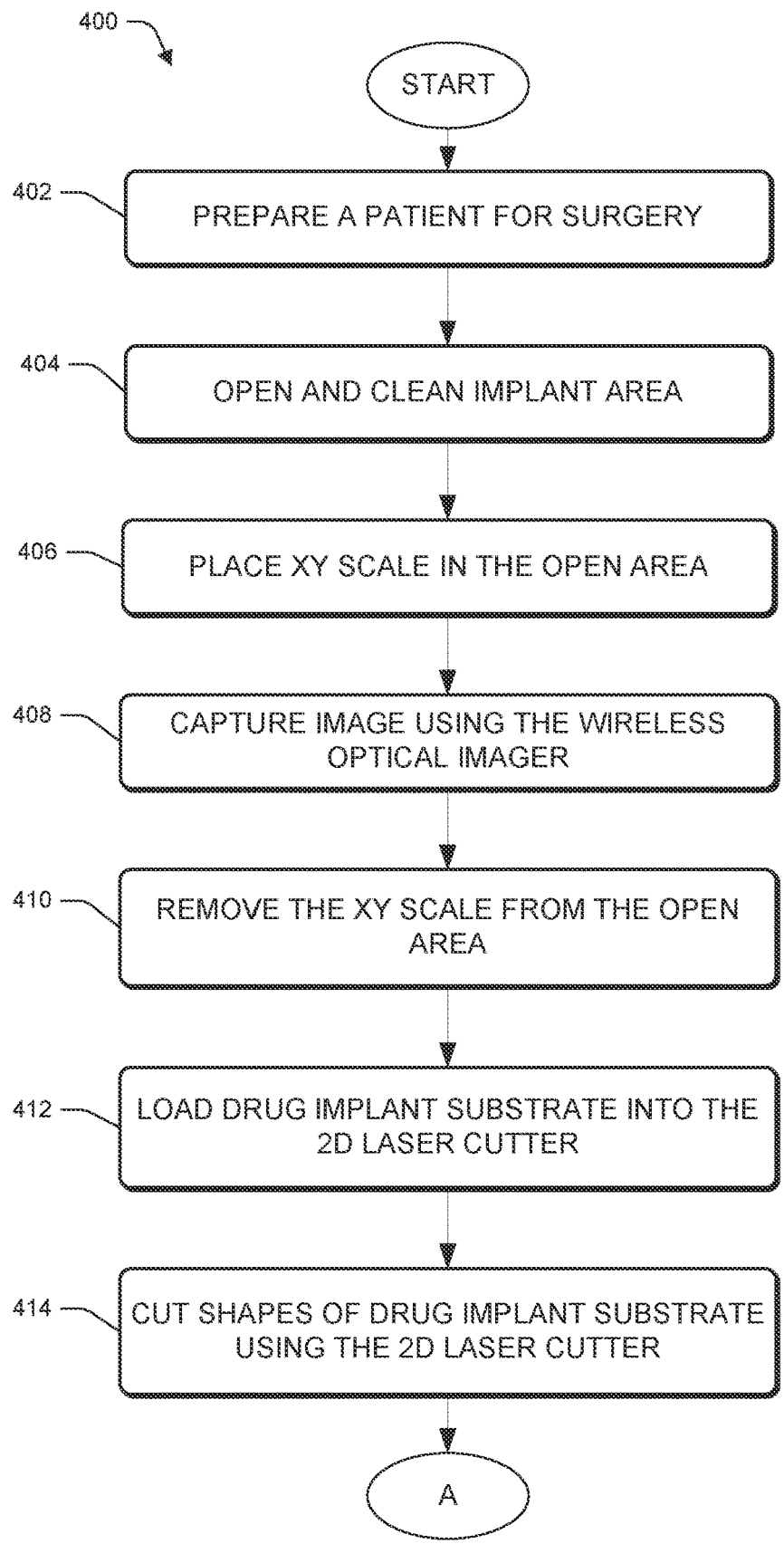
FIGS. 4A and 4B illustrate an operation method for the system, according to some embodiments.
Figure 4B:
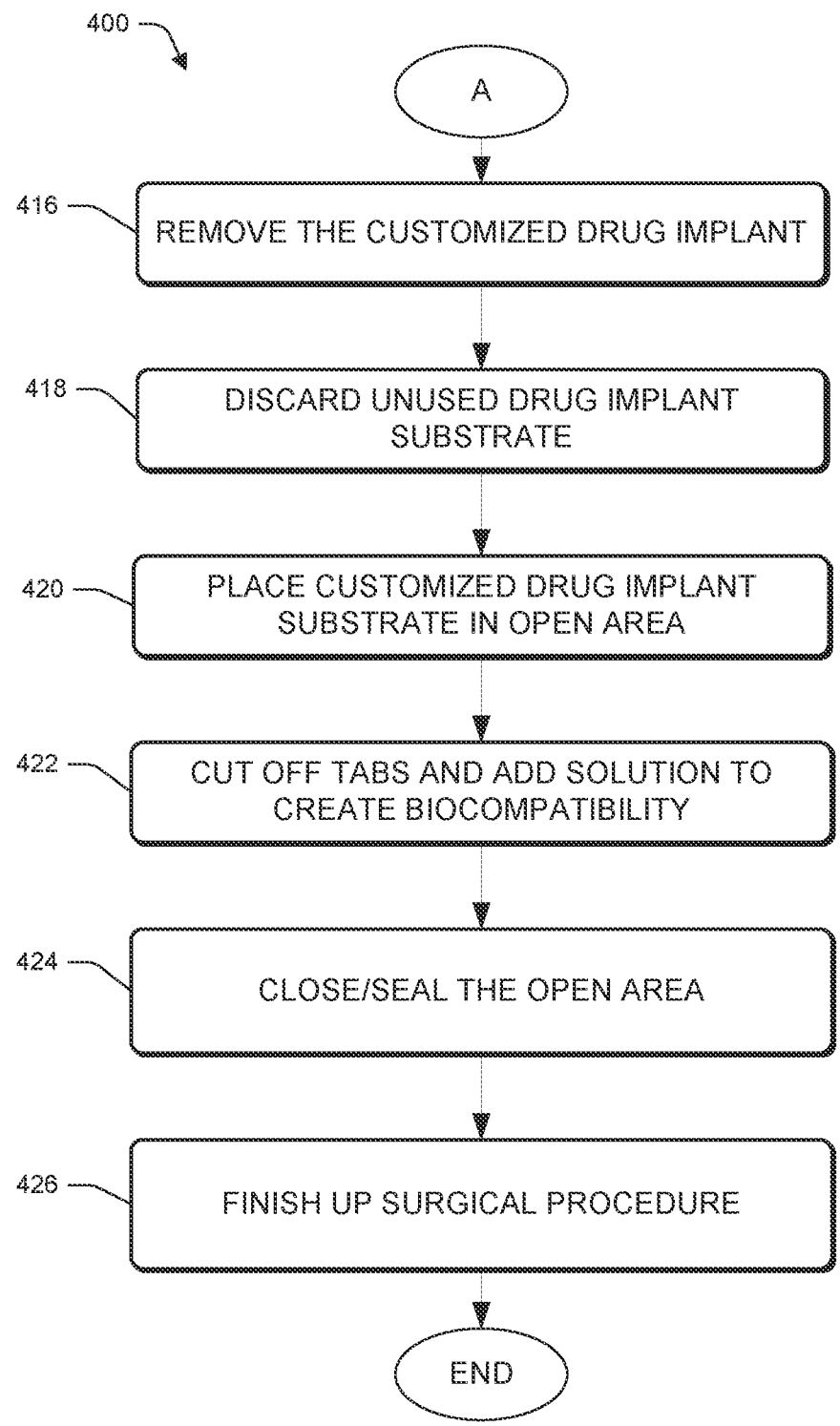

FIGS. 4A and 4B illustrate a process flow showing an operation method 400, as performed by the base module 104. FIGS. 4A and 4B illustrate steps followed during the surgical procedure according to some embodiments. FIGS. 4A and 4B are explained in conjunction with reference to FIG. 1. It should also be noted that in some alternative implementations, the functions noted in the blocks may occur out of the order noted in the drawings. For example, two blocks shown in succession in FIGS. 4A and 4B may be executed substantially concurrently or the blocks may sometimes be executed in the reverse order, depending upon the functionality involved. In addition, the process descriptions or blocks in flow charts should be understood as, in some instances, representing decisions made by a hardware structure such as a state machine.

The system 100 may prepare the patient for surgery, at step 402. Preparing the patient for the surgery may refer to performing the pre-operative procedures on the patient, including monitoring health conditions of the patient or applying anesthesia to the patient. Further, pre-operative procedures may include any minor surgery or medication for the patient, without departing from the scope of the disclosure. For example, for patient Alex, his heart rate and brain activity may be monitored for 1 day.

Further, the implant area of the patient may be opened and cleaned, at step 404. It can be noted that the implant area of the patient may be monitored and accordingly operated to be open for inserting the drug implant substrate 110. For example, for patient Alex, his front area of the brain may be opened and cleaned. At step 406, the XY scale for the 2D laser cutter 112 may be placed in the open area. The XY scale for 2D laser cutter 112 may be placed for assisting the 2D laser cutter 128 for cutting the drug implant substrate 110 to the appropriate size and shape for implantation, when placed around the open area of the patient. For example, for patient Alex, the XY scale for 2D laser cutter 112 may be placed around the identified front area of Alex's brain. Further, the system 100 may capture an image of the open area, using the wireless optical imager 116, at step 408. The image of the open area may be captured to provide proper measurements of the open area to the system 100. It can be noted that the wireless optical imager 116 may operate, as described above and capture the image of the open area of the patient. For example, the system 100 captures image—image 21 of the open area of the front part of brain for patient Alex. Further, the system 100 may remove the XY scale for 2D laser cutter 112 from the open area, at step 410. After capturing the image of the open area, the system 100 may remove the XY scale for 2D laser cutter 112. It can be noted that the role of the XY scale for 2D laser cutter 112 is to assist in providing proper measurements for the open area for insertion of the drug implant substrate 110.

At step 412, the system 100 may load the drug implant substrate 110 into the 2D laser cutter 128. It can be noted that the drug implant substrate 110 may be loaded into the 2D laser cutter 128 manually by the surgeon or by using robotic arms, if available, in the 2D laser cutter network 114. For example, for patient Alex, the drug implant substrate for insertion into the identified front area of brain of patient Alex is loaded into the 2D laser cutter 128. The drug implant substrate 110 may be selected by the surgeon or by the system 100. In some cases, the drug implant substrate 110 size and shape are known to the 2D laser cutter 128 and held for cutting.

At step 414, the system 100 may cut shapes of the drug implant substrate 110 using the 2D laser cutter 128. The system 100 may cut shapes of the drug implant substrate 110 using the 2D laser cutter 128, as per the shape of the open area. In one embodiment, the system 100 may cut shapes of the drug implant substrate 110 based on the type or dimensions of the drug implant substrate 110. It can be noted that this may result in a customized drug implant substrate 110. Further, the system 100 may add tabs to the customized drug implant substrate 110 using the tab adder 120. For example, the system 100 may cut a shape of the drug implant substrate 110 into a polygon with 6 irregular sides for inserting in the open area of patient Alex. Of course, any suitable size and 2D shape of the drug implant substrate 110 may be cut by the 2D laser cutter 128.

With reference to FIG. 4B, at step 416, the system 100 may remove the customized drug implant substrate 110 from the 2D laser cutter 128. It can be noted that the customized drug implant substrate 110 may be ready for use by the surgeon, for performing the surgical procedure on the patient. Further, the system 100 may discard the unused drug implant substrate 110, at step 418, such as the waste material that was removed during the cutting step. It can be noted that the system 100 may perform quality checks on the customized drug implant substrate 110 and may discard the unused drug implant substrate 110. In one embodiment, the system 100 may remove the previously implanted drug substrate and may discard the previously implanted drug substrate. For example, the system 100 discards the wrong sized drug implant substrate 110 or a drug implant substrate with incorrect dimensions corresponding to the patient. In some cases, the drug implant substrate is compared with the open area in the patient and an accuracy score below a threshold score may be used to determine whether to discard the drug implant substrate either before or after implanting the drug implant substrate. In some cases, where the system 100 determines an accuracy scope below a threshold, such as 90%, 80%, 70%, 60%, 50% or less, the system 100 may recommend discarding the drug implant substrate.

At step 420, the system 100 may place the customized drug implant substrate 110 in the open area in the patient. In one embodiment, the customized drug implant substrate 110 may have multiple layers. For example, in one instance, the system 100 places the polygon with 6 irregular sides of the drug implant substrate 110 in the open area of brain of patient Alex.

At step 422, the system 100 may cut off tabs and/or add solution in the open area to create biocompatibility. It can be noted that for precise fit into the open area of the patient, the system 100 may remove the tabs (e.g., 0.5 mm tabs) created by the tab adder 120. For example, the system 100 removes the tabs on the outer circumference of the drug implant substrate 110. Further, the system 100 may add a solution to the open area for creating biocompatibility by facilitating activation or germ mitigation.

Further, the system 100 may facilitate closing or sealing the open area, at step 424. After the insertion of the drug implant substrate 110 in the open area of the patient, the system 100 may close or seal the open area, using any state of art stitching techniques, without departing from the scope of the disclosure. For example, for patient Alex, after inserting the polygon with 6 irregular sides of drug implant substrate 110, Dr Van stitches the open area of brain of patient Alex. The closing of the open area may be performed robotically, manually by the surgeon, or a combination of automation and manual control and may include surgeon controlled robotics.

At step 426, the system 100 may finish up the surgical procedure, such as by performing the post-operative procedures on the patient, including monitoring health conditions of the patient. Further, post-operative procedures may include giving medication to the patient and recording the adaptation of the patient to the inserted drug implant substrate 110, without departing from the scope of the disclosure. For example, for patient Alex, his heart rate and brain activity may be monitored for 1 day.

In some embodiments, other materials could be cut such as mesh or plastic and each could be optimized from the one or more images taken of the opening in the patient. Further, these images may comprise a stack which could be cut in one operation. It can be noted that various alignment features may be added, such as a marking on the skin of a patient, or on tools or materials present in or around opening, which may align with a marking on the implant material to ensure 2D shape is properly aligned. In some embodiments, multiple marks, or registrations, may be used for providing alignment features.

Figure 5A:
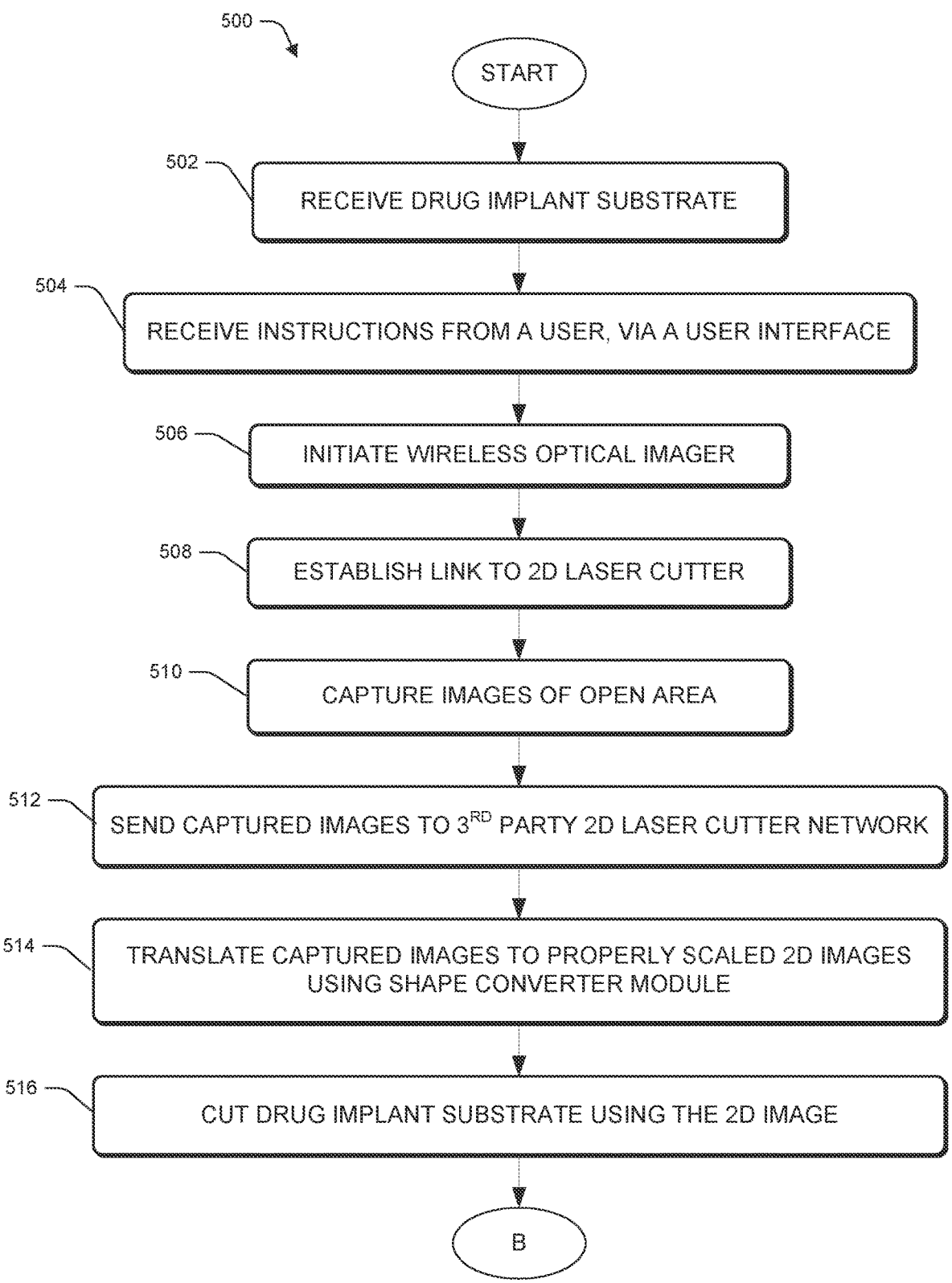
FIGS. 5A and 5B illustrate an overall method for using a 2D laser cutter of the system, according to some embodiments.
Figure 5B:
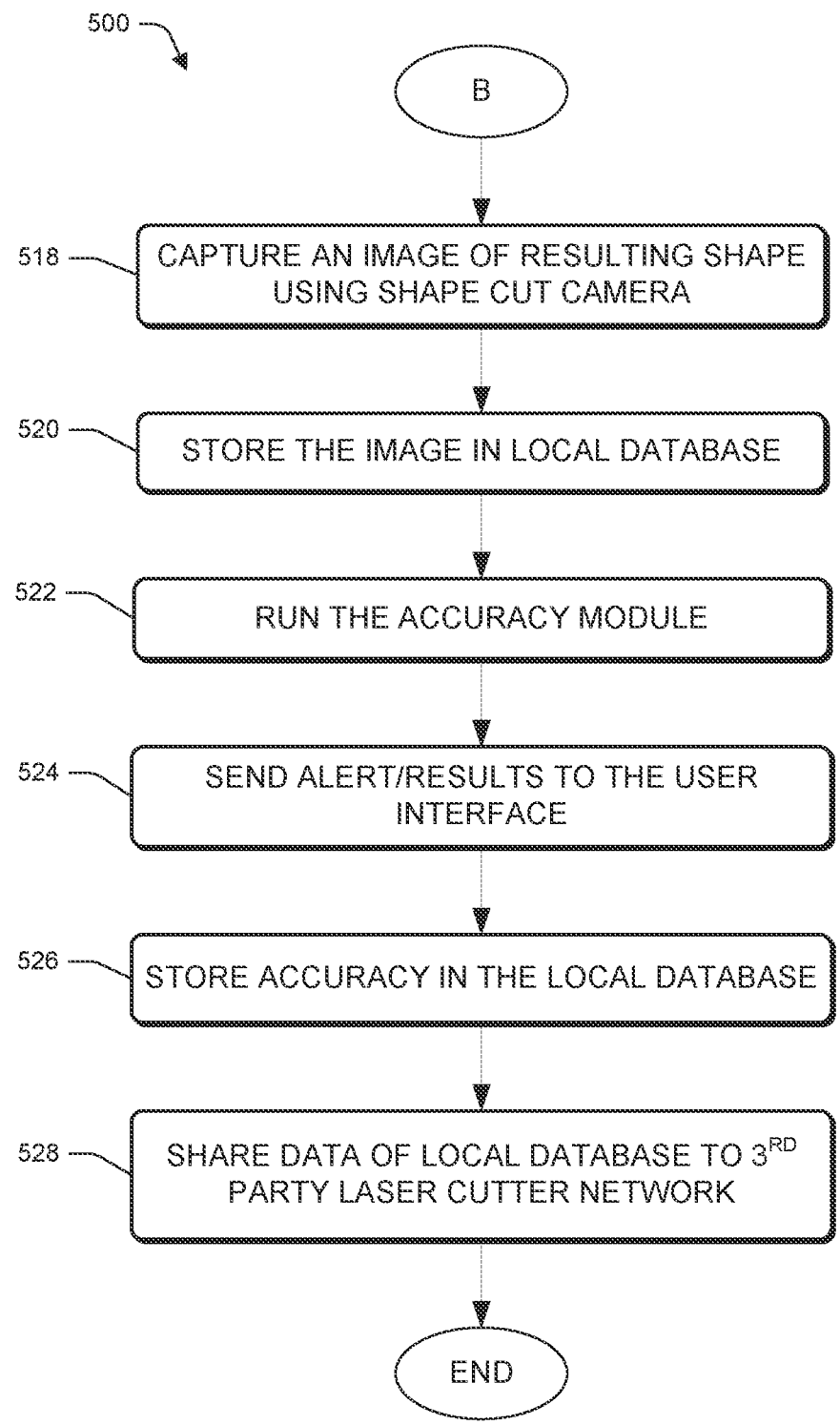

FIGS. 5A and 5B illustrate a process flow illustrating a method 500 for using the 2D laser cutter 128 according to some embodiments and may include the process being performed by the base module 104. FIGS. 5A and 5B illustrate steps followed during the surgical procedure. FIGS. 5A and 5B are explained in conjunction with FIG. 1. It should also be noted that in some alternative implementations, the functions noted in the blocks may occur out of the order noted in the drawings. For example, two blocks shown in succession in FIGS. 5A and 5B may be executed substantially concurrently or the blocks may sometimes be executed in the reverse order, depending upon the functionality involved. In addition, the process descriptions or blocks in flow charts should be understood as representing decisions made by a hardware structure such as a state machine.

At step 502, the 2D laser cutter 128 may receive the drug implant substrate 110. It can be noted that the 2D laser cutter

128 may receive the drug implant substrate 110 manually by the surgeon or by the use of robotic arms in the 2D laser cutter network 114. Further, the 2D laser cutter 128 may receive instructions from a surgeon, via the user interface 124, at step 504. Further, the surgeon may use the user interface 124 allowing the surgeon to initiate various functions. In one embodiment, the user interface 124 may comprise an imaging device to read a code (such as a QR code or other identifying information) on the drug implant substrate 110. Further, the user interface 124 may facilitate the surgeon with dictating instructions to the system 100.

At step 506, the 2D laser cutter 128 may initiate the wireless optical imager 116. It can be noted that the wireless optical imager 116 may be initiated to capture an image of the open area of the patient for performing and/or facilitating the surgical procedure. For example, the 2D laser cutter 128 may initiate the wireless optical imager 116 for capturing the image of front area of the brain of patient Alex. Further, the 2D laser cutter 128 may establish a link with the $3^{rd}$ party 2D laser cutter network 102, at step 508. It can be noted that the link with the $3^{rd}$ party 2D laser cutter network 102 may provide data from the $3^{rd}$ party 2D laser shape database 106 and may be related to measurements of the open area for performing the surgical procedure on the patient.

At step 510, the 2D laser cutter 128 may capture images of the open area, such as by using the wireless optical imager 116, at step 510. For example, the 2D laser cutter 128 captures the image of front area of the brain of patient Alex. Further, the 2D laser cutter 128 may send the captured images to the 3 rd party 2D laser cutter network 102, at step 512. For example, the 2D laser cutter 128 may send one or more images of front area of the brain of patient Alex to the $3^{rd}$ party 2D laser cutter network 102. It can be noted that the image may be saved to the local database 134.

At step 514, the 2D laser cutter 128 may translate the captured images to properly scaled 2D images, such as by using the shape converter module 118, at step 514. For example, the 2D laser cutter 128 may be configured to translate or scale the image of front area of the brain of patient Alex into a 2D shape, using the shape converter module 118. Further, the 2D laser cutter 128 may cut the drug implant substrate 110 using the 2D shape, at step 516. In some embodiments, the customized drug implant substrate 110 may reflect the shape of the opening into which the drug implant substrate 110 will be inserted. For example, the 2D laser cutter 128 may cut the drug implant substrate 110 using the 2D image of a polygon with 6 irregular sides corresponding to the shape of the open area of the patient.

At step 518, the 2D laser cutter 128 may capture an image of the resulting shape using the shape cut camera 138. It can be noted that the image of the resulting shape of the drug implant substrate 110 may be captured using the shape cut camera 138. For example, the 2D laser cutter 128 may capture image 21 of the resulting shape of the drug implant substrate 110. Further, the 2D laser cutter 128 may store the captured image in the local database 134, at step 520. It can be noted that the 2D laser cutter 128 may store the captured image in the local database 134, for future use or reference. For example, the 2D laser cutter 128 stores image 21 in the local database 134.

At step 522, the 2D laser cutter 128 may run the accuracy module 122. It can be noted that the accuracy module 122 may provide details related to the precision in cutting the drug implant substrate 110, by calculating an accuracy score. Further, the higher the accuracy score, the higher the precision in the cutting of the drug implant substrate 110. For example, for patient Alex, the accuracy score is 96%. In some cases, where the accuracy score is below a threshold value, an alert may be provided to the surgeon noting the accuracy score below a threshold score. The surgeon, or the system 100, may determine to cut another drug implant substrate 110, which may take into account the rejected drug implant substrate 110 to calculate and cut a subsequent drug implant substrate 110. At step 524, the 2D laser cutter 128 may send alerts or results to the user interface 124. Based on the calculation performed by the accuracy module 122, the 2D laser cutter 128 may send the accuracy score to the user interface 124. For example, the 2D laser cutter 128 sends the accuracy score of 96% for patient Alex, to the user interface 124.

At step 526, the 2D laser cutter 128 may store the accuracy score in the local database 134. For example, the 2D laser cutter 128 stores the accuracy score of 96% for patient Alex, in the local database 134. Further, the 2D laser cutter 128 may share the data of the local database 134 to the $3^{rd}$ party 2D laser cutter network 102, at step 528. For example, the 2D laser cutter 128 shares the data of the local database 134 that accuracy score of 96% for patient Alex to the $3^{rd}$ party 2D laser cutter network 102. Further, it can be noted that the disclosure describes the use of Gliadel wafer, but may be used for other types of implants, not limiting to, customization of implants for treatment of other types of cancers, stomach ulcers, delivery of slow release medications such as to treat chronic pain. In an additional embodiment, an electric implant which has zones, similar to LED light strips, where an implant may be customized by cutting along suitable cutting zones. In some embodiments, the 2D laser cutter 128 may additionally etch some traces on an electrical implant to control the manner in which an electrical stimulus is applied.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as disclosed above.

The disclosure sets forth example embodiments and, as such, is not intended to limit the scope of embodiments of the disclosure and the appended claims in any way. Embodiments have been described above with the aid of functional building blocks illustrating the implementation of specified functions and relationships thereof. The boundaries of these functional building blocks have been arbitrarily defined herein for the convenience of the description. Alternate boundaries can be defined to the extent that the specified functions and relationships thereof are appropriately performed.

The foregoing description of specific embodiments will so fully reveal the general nature of embodiments of the disclosure that others can, by applying knowledge of those of ordinary skill in the art, readily modify and/or adapt for various applications such specific embodiments, without undue experimentation, without departing from the general concept of embodiments of the disclosure. Therefore, such adaptation and modifications are intended to be within the meaning and range of equivalents of the disclosed embodiments, based on the teaching and guidance presented herein. The phraseology or terminology herein is for the purpose of description and not of limitation, such that the terminology or phraseology of the specification is to be interpreted by persons of ordinary skill in the relevant art in light of the teachings and guidance presented herein.

The breadth and scope of embodiments of the disclosure should not be limited by any of the above-described example embodiments but should be defined only in accordance with the following claims and their equivalents.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

Unless otherwise noted, the terms "connected to" and "coupled to" (and their derivatives), as used in the specification, are to be construed as permitting both direct and indirect (i.e., via other elements or components) connection. In addition, the terms "a" or "an," as used in the specification, are to be construed as meaning "at least one of." Finally, for ease of use, the terms "including" and "having" (and their derivatives), as used in the specification and annexed drawings disclose examples of systems, apparatus, devices, and techniques that may provide medical patient interaction and assessment. It is, of course, not possible to describe every conceivable combination of elements and/or methods for purposes of describing the various features of the disclosure, but those of ordinary skill in the art recognize that many further combinations and permutations of the disclosed features are possible. Accordingly, various modifications may be made to the disclosure without departing from the scope or spirit thereof. Further, other embodiments of the disclosure may be apparent from consideration of the specification and annexed drawings, and practice of disclosed embodiments as presented herein. Examples put forward in the specification and annexed drawings should be considered, in all respects, as illustrative and not restrictive. Although specific terms are employed herein, they are used in a generic and descriptive sense only, and not used for purposes of limitation.

Those skilled in the art will appreciate that, in some implementations, the functionality provided by the processes and systems discussed above may be provided in alternative ways, such as being split among more software programs or routines or consolidated into fewer programs or routines. Similarly, in some implementations, illustrated processes and systems may provide more or less functionality than is described, such as when other illustrated processes instead lack or include such functionality respectively, or when the amount of functionality that is provided is altered. In addition, while various operations may be illustrated as being performed in a particular manner (e.g., in serial or in parallel) and/or in a particular order, those skilled in the art will appreciate that in other implementations the operations may be performed in other orders and in other manners. Those skilled in the art will also appreciate that the data structures discussed above may be structured in different manners, such as by having a single data structure split into multiple data structures or by having multiple data structures consolidated into a single data structure. Similarly, in some implementations, illustrated data structures may store more or less information than is described, such as when other illustrated data structures instead lack or include such information respectively, or when the amount or types of information that is stored is altered. The various methods and systems as illustrated in the figures and described herein represent example implementations. The methods and systems may be implemented in software, hardware, or a combination thereof in other implementations. Similarly, the order of any method may be changed, and various elements may be added, reordered, combined, omitted, modified, etc., in other implementations.

The processor(s) as disclosed herein can be configured with instructions to perform any one or more steps of any method as disclosed herein, including issuing instructions to one or more pieces of hardware to aid in the surgical techniques described herein.

From the foregoing, it will be appreciated that, although specific implementations have been described herein for purposes of illustration, various modifications may be made without deviating from the spirit and scope of the appended claims and the elements recited therein. In addition, while certain aspects are presented below in certain claim forms, the inventors contemplate the various aspects in any available claim form. For example, while only some aspects may currently be recited as being embodied in a particular configuration, other aspects may likewise be so embodied. Various modifications and changes may be made as would be obvious to a person skilled in the art having the benefit of this disclosure. It is intended to embrace all such modifications and changes and, accordingly, the above description is to be regarded in an illustrative rather than a restrictive sense.

What is claimed is:

1. A system for implanting surgical material in a patient's body, the system comprising:
   a laser cutter network comprising:
      a laser cutter; and
      a processor configured with instructions that, when executed by the processor, cause the processor to perform the steps of:
         capturing, with an imaging device, an image of an open area of the patient's body and an XY scale adjacent the open area of the patient's body;
         creating, based at least in part on the captured image, a two-dimensional profile associated with the open area of the patient's body;
         modifying the two-dimensional profile by adding one or more tabs at discrete locations along the two-dimensional profile, the one or more tabs expanding the two-dimensional profile at the discrete locations;
         creating, with the laser cutter and based at least in part on the captured image, a customized implant substrate corresponding to the two-dimensional profile and the one or more tabs;
         placing the customized implant substrate in the open area of the patient's body; and
         sealing the open area, after placing the customized implant substrate in the open area.

2. The system as in claim 1, wherein creating the implant substrate comprises shaping the implant substrate using the laser cutter.

3. The system as in claim 1, wherein the instructions further cause the processor to determine an accuracy score for the customized implant substrate.

4. The system as in claim 3, further comprising determining that the accuracy score is above a threshold score.

5. The system as in claim 1, further comprising a communication link to a laser cutter network and wherein the system is configured to retrieve, via the network, a cut profile.

6. The system as in claim 5, wherein the instructions further cause the processor to actuate the laser cutter to shape the implant substrate according to the cut profile.

7. The system as in claim 1, wherein creating the implant substrate comprises cutting the implant substrate to include the one or more tabs.

8. The system as in claim 7, wherein the instructions further cause the processor to actuate the laser cutter to remove the one or more tabs from the implant substrate.

9. The system as in claim 1, wherein the instructions further cause the processor to scale the image based at least in part on an XY scale displayed in the image.

10. The system as in claim 1, further comprising an additive manufacturing system and wherein creating the customized implant substrate comprises actuating the additive manufacturing system.

11. A surgical method, under control of one or more processors, comprising:
    opening and cleaning an implant area within a patient;
    capturing, with an imaging device, an image of the implant area and the XY scale;
    creating, based at least in part on the image of the implant area, a profile for an implant substrate;
    modifying the profile for the implant substrate by adding one or more tabs at discrete locations along the profile, the tabs expanding the profile at the discrete locations;
    cutting, based at least in part on the profile and with a laser cutter, the implant substrate to include the one or more tabs at the discrete locations along the profile;
    positioning the implant substrate into the implant area within the patient; and
    closing the implant area within the patient.

12. The surgical method as in claim 11, wherein the implant substrate is one or more of a drug implant substrate, prosthetic substrate, structural biologics substrate, or an antibiotic substrate.

13. The surgical method as in claim 11, further comprising the step of loading the implant substrate into the laser cutter prior to cutting the implant substrate.

14. The surgical method as in claim 11, wherein the step of cutting the implant substrate includes cutting around the one or more tabs.

15. The surgical method as in claim 11, further comprising the step of adding a solution to the implant substrate to create biocompatibility between the implant substrate and the patient.

16. The surgical method as in claim 11, further comprising the step of establishing a communications link between the one or more processors and a laser cutter network and retrieving, from the laser cutter network a cut profile.

17. The surgical method as in claim 11, further comprising the step of scaling the captured image to create a scaled image and cutting, with the laser cutter, the implant substrate based at least in part on the scaled image.

18. The surgical method as in claim 11, further comprising the step of capturing, with the imaging device, a second image that displays the implant substrate and the implant area.

19. The surgical method as in claim 18, further comprising the step of determining an accuracy score between the implant substrate and the implant area and displaying the accuracy score on a user interface.

* * * * *